United States Patent
Lee et al.

(10) Patent No.: US 8,974,385 B2
(45) Date of Patent: Mar. 10, 2015

(54) METHOD AND APPARATUS FOR PROVIDING BLOOD GLUCOSE MANAGEMENT INFORMATION

(75) Inventors: Kwang-hyeon Lee, Seoul (KR); Kyu-tae Yoo, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 530 days.

(21) Appl. No.: 12/824,344

(22) Filed: Jun. 28, 2010

(65) Prior Publication Data

US 2011/0071365 A1 Mar. 24, 2011

(30) Foreign Application Priority Data

Sep. 23, 2009 (KR) .................. 10-2009-0090227

(51) Int. Cl.
*A61B 5/00* (2006.01)
*G06F 19/00* (2011.01)
*A61B 5/145* (2006.01)

(52) U.S. Cl.
CPC ......... *G06F 19/3443* (2013.01); *A61B 5/14532* (2013.01); *G06F 19/3418* (2013.01)
USPC .......................................... 600/300; 702/179

(58) Field of Classification Search
USPC ............... 600/300, 301, 319; 702/19
See application file for complete search history.

(56) References Cited

U.S. PATENT DOCUMENTS

| | | | |
|---|---|---|---|
| 7,774,145 B2 * | 8/2010 | Brauker et al. .................. 702/19 |
| 7,783,442 B2 * | 8/2010 | Mueller et al. .................. 702/85 |
| 8,285,487 B2 * | 10/2012 | Bergstrom et al. ............. 702/19 |
| 2003/0208113 A1 * | 11/2003 | Mault et al. ................... 600/316 |
| 2004/0162678 A1 * | 8/2004 | Hetzel et al. .................... 702/19 |
| 2005/0038332 A1 * | 2/2005 | Saidara et al. ................ 600/347 |
| 2005/0113653 A1 * | 5/2005 | Fox et al. ....................... 600/300 |
| 2005/0159656 A1 | 7/2005 | Hockersmith et al. |
| 2007/0179352 A1 * | 8/2007 | Randlov et al. ............... 600/300 |
| 2008/0114215 A1 * | 5/2008 | Ward et al. .................... 600/300 |
| 2008/0183060 A1 * | 7/2008 | Steil et al. ..................... 600/365 |
| 2008/0194924 A1 * | 8/2008 | Valk et al. ..................... 600/301 |
| 2009/0006061 A1 * | 1/2009 | Thukral et al. ................ 703/11 |
| 2009/0018779 A1 * | 1/2009 | Cohen et al. .................... 702/19 |
| 2009/0036753 A1 * | 2/2009 | King ............................ 600/301 |
| 2009/0118589 A1 * | 5/2009 | Ueshima et al. ............. 600/300 |
| 2009/0157430 A1 * | 6/2009 | Rule et al. ........................ 705/3 |
| 2009/0163781 A1 * | 6/2009 | Say et al. ...................... 600/301 |
| 2009/0240127 A1 * | 9/2009 | Ray .............................. 600/365 |
| 2009/0299152 A1 * | 12/2009 | Taub et al. .................... 600/300 |
| 2010/0075353 A1 * | 3/2010 | Heaton ........................... 435/14 |
| 2010/0113892 A1 * | 5/2010 | Kaput et al. .................. 600/301 |
| 2010/0125241 A1 * | 5/2010 | Prud'homme et al. ......... 604/65 |
| 2010/0145174 A1 * | 6/2010 | Alferness et al. ............ 600/365 |
| 2010/0222648 A1 * | 9/2010 | Tan .............................. 600/301 |

FOREIGN PATENT DOCUMENTS

| | | |
|---|---|---|
| JP | 2009-037588 A | 2/2009 |
| KR | 1020070063195 A | 6/2007 |
| WO | 2005/093629 A2 | 10/2005 |

* cited by examiner

*Primary Examiner* — William Thomson
*Assistant Examiner* — Bobby Soriano
(74) *Attorney, Agent, or Firm* — Cantor Colburn LLP

(57) ABSTRACT

An apparatus and method of providing blood glucose management information includes a determination unit that determines a similarity of a blood glucose change pattern of a user by comparing blood glucose information obtained from the user and stored blood glucose information, an extraction unit that extracts at least one piece of blood glucose information from the stored blood glucose information according to the similarity and generates extracted blood glucose information, and an interface unit which provides the blood glucose management information, which corresponds to the extracted blood glucose information, to the user.

18 Claims, 6 Drawing Sheets

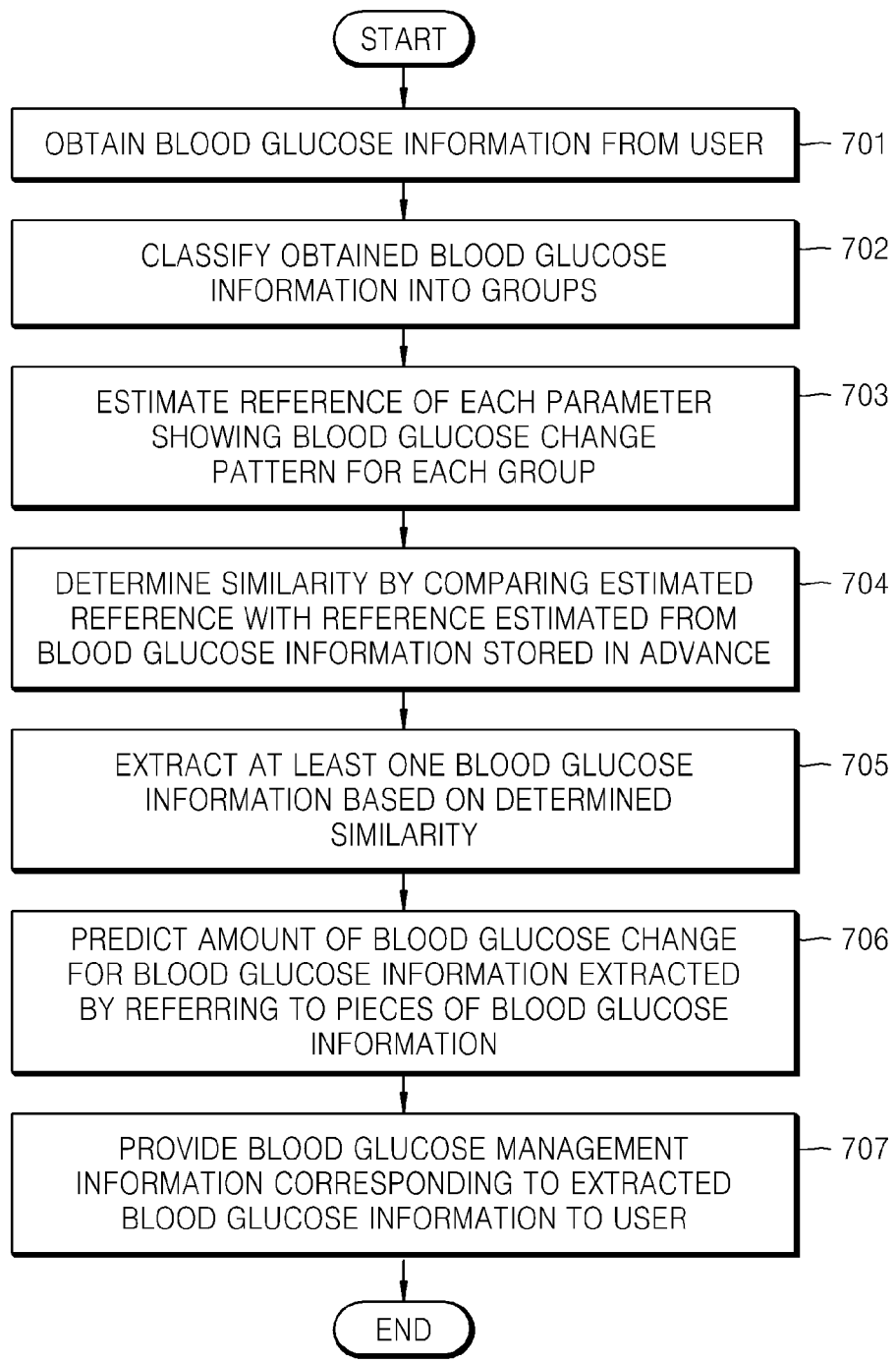

METHOD AND APPARATUS FOR PROVIDING BLOOD GLUCOSE MANAGEMENT INFORMATION

CROSS-REFERENCE TO RELATED APPLICATION

This application claims priority to Korean Patent Application No. 10-2009-0090227, filed on Sep. 23, 2009, and all the benefits accruing therefrom under 35 U.S.C. §119, the content of which in its entirety is herein incorporated by reference.

BACKGROUND

1) Field

The general inventive concept relates to a method and apparatus for providing blood glucose management information to a user and, more particularly, the general inventive concept relates to a method and apparatus for providing blood glucose management information to provide an appropriate treatment by searching for blood glucose information having a similar blood glucose change pattern.

2) Description of the Related Art

Diabetes is a chronic disease in which patients need to continuously monitor their blood glucose and receive treatment using an appropriate drug, exercise and dietary prescription, for example, according to changes of their blood glucose levels. To reduce medical expenses, a home health care service has recently been developed to reduce a required number of visits to hospitals while continuously monitoring blood glucose information of a patient. The home health care service typically includes a service, called a home tele-monitoring service, for remote management of a patient, at the patient's home, by a medical professional. A device, called a home tele-monitoring device, is installed at the patient's home and for connecting the patient to a physician. In addition, a high-quality patient management service may be provided, using evidence-based medicine that provides a medical service using information collected by the home tele-monitoring service.

SUMMARY

The general inventive concept includes a method and apparatus for providing blood glucose management information of a patient to provide an appropriate treatment for the patient by searching for blood glucose information having a similar blood glucose change pattern.

The general inventive concept also includes a computer-readable recording medium in which a program for implementing the method is stored.

Provided is a method of providing blood glucose management information, the method including: determining a similarity of a blood glucose change pattern of a user by comparing blood glucose information obtained from the user and stored blood glucose information; extracting at least one piece of blood glucose information from the stored blood glucose information according to the similarity to generate extracted blood glucose information; and providing the blood glucose management information, which corresponds to the extracted blood glucose information, to the user.

Provided also is a computer program product comprising a computer-readable computer program for executing a method of providing blood glucose management information and instructions for causing a computer to implement the method, the method comprising: determining a similarity of a blood glucose change pattern of a user by comparing blood glucose information obtained from the user and stored blood glucose information; extracting at least one piece of blood glucose information from the stored blood glucose information according to the similarity to generate extracted blood glucose information; and providing the blood glucose management information, which corresponds to the extracted blood glucose information, to the user.

Also provided is an apparatus that provides blood glucose management information, the apparatus including: a determination unit that determines a similarity of a blood glucose change pattern of a user by comparing blood glucose information obtained from the user and stored blood glucose information; an extraction unit that extracts at least one piece of blood glucose information from the stored blood glucose information according to the similarity and generates extracted blood glucose information; and an interface unit that provides the blood glucose management information, which corresponds to the extracted blood glucose information, to the user.

BRIEF DESCRIPTION OF THE DRAWINGS

The above and/or other aspects of the general inventive concept will become more readily apparent from the following detailed description, taken in conjunction with the accompanying drawings, in which:

FIG. 7 is a flowchart illustrating an embodiment of a method of providing blood glucose management information.

DETAILED DESCRIPTION

Figure 1:
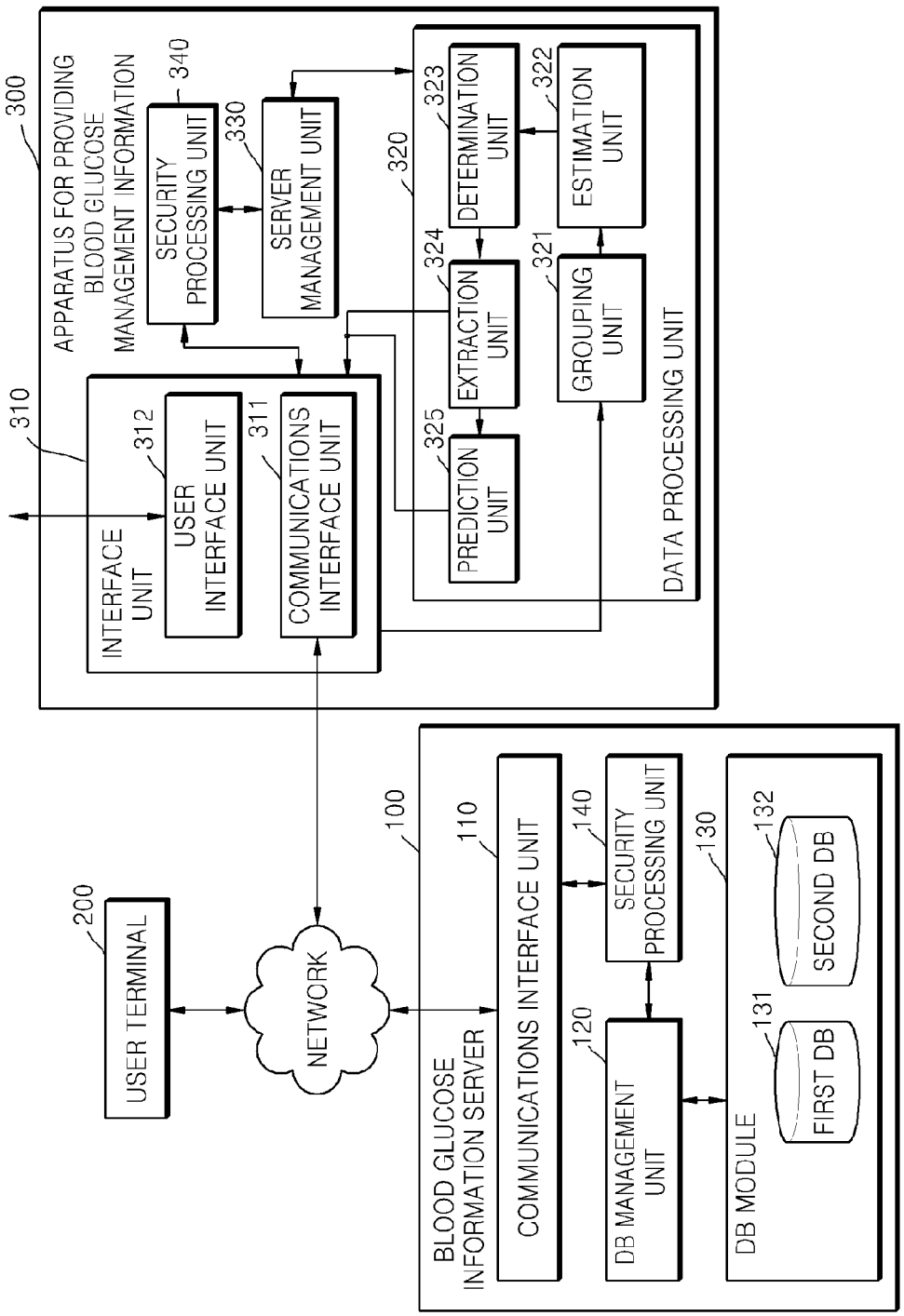
FIG. 1 is a block diagram of an embodiment of a blood glucose management providing system.

The general inventive concept now will be described more fully with reference to the accompanying drawings, in which various example embodiments are shown. The general inventive concept may, however, be embodied in many different forms, and should not be construed as limited to the example embodiments set forth herein. Rather, these example embodiments are provided so that this disclosure will be thorough and complete, and will fully convey the scope of the general inventive concept to those of ordinary skill in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, example embodiments of the general inventive concept will be described in further detail with reference to the accompanying drawings.

FIG. 1 is a block diagram of an embodiment of a blood glucose management information providing system. As shown in FIG. 1, the blood glucose management information providing system includes a blood glucose information server 100, a user terminal 200 and an apparatus, e.g., a part, for providing blood glucose management information 300. The user terminal 200 is connected to the blood glucose information server 100 and the apparatus for providing blood glucose management information 300. However, it will be noted that, in one or more additional embodiments, a plurality of the user terminals 200 may be connected to the blood glucose information server 100 and the apparatus for providing blood glucose management information 300.

The blood glucose information server 100, the user terminal 200, and the apparatus for providing blood glucose management information 300 may be connected to each other via a wired and/or a wireless network. Specifically, for example, the network may be the Internet, a local area network ("LAN"), a wireless LAN ("WLAN") or a wide area network ("WAN"), for example, but is not limited thereto, and any type of network capable of transceiving information, e.g., sending and receiving information, may also be used.

In an embodiment, the user terminal 200 may be an external device that is connected via a wired or wireless network to transmit and receive data to and from the blood glucose information server 100 and the apparatus for providing blood glucose management information 300. Specifically, the user terminal 200 may include any device connected to the apparatus for providing blood glucose management information 300 to input data by a user or output processed data to the user. More specifically, for example, the user terminal 200 may include a blood glucose sensor, a health information terminal, a computer system, a personal digital assistant ("PDA"), a cellular phone and a home tele-monitoring device, but additional embodiments are not limited thereto.

In addition, as used herein, a "user" indicates someone, e.g., a subject, who uses the user terminal 200 and the apparatus for providing blood glucose management information 300, including a subject whose blood glucose is measured, as well as a medical professional managing the health condition of the subject. In this regard, the subject may be a patient having diabetes, for example, but is not limited thereto. The subject may also be any user who uses the apparatus for providing blood glucose management information 300 to manage a blood glucose level. The medical professional is generally a doctor, e.g., a physician, or a nurse with professional medical knowledge, but is not limited thereto, and may also be any person providing a health managing service.

In an embodiment, the blood glucose information server 100, the user terminal 200, and the apparatus for providing blood glucose management information 300 are separate devices connected to each other via a network, but it will be understood that the abovementioned components may be integrated into one or two devices or, alternatively, may be subdivided into more than three devices. For example, the apparatus for providing blood glucose management information 300 may include a part of, or the entire function of, the blood glucose information server 100. Likewise, the user terminal 200 may include a part of, or the entire function of, the apparatus for providing blood glucose management information 300.

The blood glucose management information providing system of FIG. 1 only shows elements related to providing information for managing blood glucose. Accordingly, it will be understood by one of ordinary skill in the art that the blood glucose management information providing system of FIG. 1 may also include other elements that are commonly used in the art.

As used herein, "blood glucose" or "blood glucose level" indicates a concentration of glucose in blood, and "blood glucose information" includes blood glucose level, as well as information related to factors influencing the blood glucose level. Specifically, for example, information related to factors influencing the blood glucose includes physical traits of a user, e.g., a subject, whose blood glucose is measured, times when the subject eats, times when the blood glucose of the subject is measured, ingredients of food eaten by the subject, amounts of food eaten by the subject, nutritional and other characteristics of food eaten by the subject, information relevant to insulin infusion into the subject, and information related to a blood glucose-controlling drug of the subject, but is not limited to the foregoing list. In an embodiment, the physical traits of a subject include information indicating the personal physical state of the subject such as height, weight, gender, age and the degree of muscle mass, a variety of historical records of the subject such as medical history, family disease history, drug administration and insulin infusion history, occupation, sensitivity to stress, as well as amount and level of exercise, for example. Thus, the blood glucose information includes all information related to measuring and predicting blood glucose, and treating blood glucose-related diseases.

Referring still to FIG. 1, the blood glucose information server 100 includes a communications interface unit 110, a database ("DB") management unit 120, a database module 130 and a security processing unit 140. The communications interface unit 110 transmits and receives data to and from the user terminal 200 and the apparatus for providing blood glucose management information 300 via a wired or a wireless network.

The database management unit 120 manages a first database 131 and a second database 132 of the database module 130. For example, the database management unit 120 renews the first database 131 and the second database 132, or extracts data requested by the apparatus for providing blood glucose management information 300 from the first database 131 and the second database 132. The database management operates with the apparatus for providing blood glucose management information 300, but may be independently performed in the database management unit 120. In an embodiment, for example, the operation between the database management unit 120 and the apparatus for providing blood glucose management information 300 indicates that the apparatus for providing blood glucose management information 300 renews data in the first database 131 and/or the second database 132, or extracts data therefrom, by referring to data stored in the database module 130. The method of managing a database will be described in further detail below with reference to a server management unit 330 of the apparatus for providing blood glucose management information 300.

Still referring to FIG. 1, the database module 130 includes the first database 131 and the second database 132 in which pieces, e.g. portions or individual data/information, of blood glucose information are stored. The pieces of blood glucose information include not only blood glucose information of the user, but also blood glucose information of others, e.g., other users or other persons, whose blood glucose and/or other characteristics have been measured.

In an embodiment, the first database 131 stores raw data of the pieces of blood glucose information and raw data of blood glucose management information corresponding to the pieces of blood glucose information, and the second database 132 stores data obtained by processing, e.g., by referring to the raw data stored in the first database 131. The processed data stored in the second database 132 is prepared by processing data to include the content of the blood glucose data stored in the first database 131.

In an embodiment, blood glucose management information corresponding to the blood glucose information of the first database 131 indicates a blood glucose management record of a subject indicated by the blood glucose information. For example, the blood glucose management record includes a blood glucose level including time information, as well as detailed information regarding blood glucose changes according to insulin infusion, blood glucose-controlling drug administration, exercise and food intake, for example.

The processed data stored in the second database 132 may include one or more of a reference estimated with respect to the blood glucose information stored in the first database 131, a reference estimated with respect to each parameter of a plurality of parameters showing a blood glucose change pattern, a reference estimated with respect to groups classified according to times when the blood glucose level is measured, and/or which are relevant to times when a factor influencing blood glucose is generated, and a reference estimated with respect to each of the parameters according to the groups. The method of estimating the reference that is processed data stored in the second database 132 will be described in greater detail below with reference to an estimation unit 322 of the apparatus for providing blood glucose management information 300.

The database module 130 (FIG. 1) stores blood glucose information of various users, and may store such information in advance of a particular user measuring their blood glucose level. In an embodiment, users include patients having blood glucose-related diseases, and also subjects who simply want to manage their blood glucose, regardless of whether they may have blood glucose-related disease. As discussed above, the first database 131 includes raw data of pieces of blood glucose information of various users, and the second database 132 includes data processed by referring to the raw data of the first database 131. In an embodiment, the data stored in the first database 131 may be renewed, e.g., may be replaced, refreshed, or updated, based on the blood glucose information obtained from the users, and the data stored in the second database 132 may also be renewed based on the data renewed by the first database 131. The abovementioned renewals may be performed automatically and/or manually by the user.

The database module 130 stores blood glucose information. In general, a subject's blood glucose is influenced not only by factors such as exercise, food intake and administration of medicine, but also by physical characteristics of the subject. To manage this blood glucose influenced by various factors, an evidence-based treatment for providing a medical service, based on the blood glucose management record of the subject, is needed. In addition, in an embodiment, the data stored in the database module 130 is efficiently used for extracting data used in the evidence-based treatment.

Still referring to FIG. 1, the security processing unit 140 implements, e.g., performs, a security process on data outputted to the communications interface unit 110 and/or inputted from the communications interface unit 110. More specifically, for example, the security processing unit 140 may encode data outputted to the communications interface unit 110, such as the blood glucose information of the subject and the blood glucose management information, and convert the subject's identification information, such as the real name of the subject among the blood glucose information and the blood glucose management information, into symbols such as numbers and characters, which are unrecognizable as the real name of the user and the associated blood glucose management information. The security processing unit 140 may also decode data inputted to the communications interface unit 110, such as encoded data received from the user terminal 200 or the apparatus for providing blood glucose management information 300. In an additional embodiment, the blood glucose information server 100 may not include the security processing unit 140.

As shown in FIG. 1, the apparatus for providing blood glucose management information 300 includes an interface unit 310, a data processing unit 320, the server management unit 330 and a security processing unit 340.

The interface unit 310 receives blood glucose information from the user and provides blood glucose management information that corresponds to blood glucose information similar to the received blood glucose information. In an embodiment, the blood glucose information obtained from the user may be stored in the first database 131 of the blood glucose information server 100 by the server management unit 330.

The interface unit 310 includes a communications interface unit 311 and a user interface unit 312. The communications interface unit 311 receives blood glucose information from the user terminal 200 and transmits blood glucose management information corresponding to blood glucose information similar to the received blood glucose information to the user terminal 200.

Thus, the user of the user terminal 200 may search for a blood glucose change pattern of the subject whose blood glucose levels have been measured by referring to the blood glucose management information. More particularly, information for managing blood glucose may be obtained by referring to a degree of blood glucose change of the subject according to a diet or a blood glucose-controlling drug of the subject.

The user interface unit 312 receives blood glucose information from the user, which may be the subject, and outputs blood glucose management information corresponding to blood glucose information, similar to the received blood glucose information, to the user. The user inputs blood glucose information by manipulating the user interface unit 312, and then blood glucose information corresponding to blood glucose similar to the inputted blood glucose information may be outputted to the user via the user interface unit 312.

In one or more embodiments, for example, the user interface unit 312 includes an input/output device, such as a display panel, a mouse, a keyboard, a touch screen, a monitor and/or a speaker mounted in the apparatus for providing blood glucose management information 300, but additional embodiments are not limited thereto.

As described above, the blood glucose management information includes a detailed blood glucose management record of the subject indicating the degree of blood glucose change according to insulin, food intake and exercise, for example. Thus, the user may appropriately treat a patient, e.g., the subject, having blood glucose to be managed with reference to the blood glucose management information provided by the apparatus for providing blood glucose management information 300. In addition, the blood glucose management information includes data related to factors that influence the blood glucose and that has been collected for a period of time. Thus, changes of references collected for a long, e.g., extended, period of time for various parameters indicating the blood glucose change pattern may be represented by a graph and/or a table. Thus, the user is able to recognize an overall trend of a blood glucose change pattern represented by the table and/or the graph using the interface unit 310. In addition, the interface unit 310 provides information related to a blood glucose change pattern, which is aligned according to a similarity to the blood glucose information of the user.

The apparatus for providing blood glucose management information 300 may obtain blood glucose information from the user terminal 200, using the communications interface unit 311, or may receive blood glucose information from the user using the user interface unit 312. The apparatus for providing blood glucose management information 300 may transmit blood glucose management information corresponding to blood glucose information similar to the obtained blood glucose information to the user terminal 200 and then output the same to the user terminal 200, or may output the blood glucose management information to the user of the apparatus for providing blood glucose management information 300.

The user, e.g., a subject, may search for blood glucose information similar to the blood glucose information measured using a home tele-monitoring device at home using the user terminal 200, and another user, e.g., a medical professional, may search for blood glucose information similar to the blood glucose of a person who wants to manage their health state at a hospital using a computer system as a user terminal 200, for example. Thus, the user directly inputs blood glucose information to the apparatus for providing blood glucose management information 300 to search for blood glucose information similar to the input blood glucose information. In addition, the user conveniently searches for blood glucose information using various methods as described above and refer to blood glucose management information corresponding to the found similar blood glucose information so that an accurate medical service is provided.

The data processing unit 320 processes data related to the blood glucose information. Still referring to FIG. 1, the data processing unit 320 includes a grouping unit 321, the estimation unit 322, a determination unit 323, an extraction unit 324 and a prediction unit 325.

The grouping unit 321 classifies blood glucose information obtained from the user into several groups, according to times when the blood glucose is measured, which are also related to times when factors influencing blood glucose are generated. In an embodiment, the factors influencing blood glucose include when the subject eats, the ingredients/amount of food eaten, the amount of carbohydrate contained in the food, intensity/load of exercise, intensity/amount of stress, degree of insulin infusion and/or types of blood glucose-controlling drugs, for example. However, additional embodiments are not limited the abovementioned factors, and any factor that may influence the blood glucose may be used.

For purposes of description hereinafter, the factors influencing blood glucose will be described with reference to when the subject eats, but it will be noted that additional embodiments are not limited thereto. Thus, in an example embodiment described in greater detail below, the grouping unit 321 classifies the blood glucose information into at least one group according to mealtimes of the subject.

Specifically, for example, food intake may be classified into meals and snacks, and meals may be further classified into breakfast, lunch and dinner, for example. The grouping unit 321 may add a tag, indicating the group, e.g., a classified time zone, of the measured blood glucose referring to the obtained blood glucose information. More particularly, the measured blood glucose level may be classified into a fasting glucose, blood glucose before/after breakfast, blood glucose before/after lunch, and blood glucose before/after dinner. In an embodiment, definitions of before and after each meal is set by the apparatus for providing blood glucose management information 300, but may be changed by the user.

The grouping unit 321 may obtain the mealtime and time when the blood glucose is measured from the user and classify the blood glucose based on the obtained information, as described above. However, this process is not limited thereto, and the user may directly input the above information. Specifically, the user may input the measured blood glucose level and classification information of the blood glucose level, e.g., blood glucose within 4 hours after a meal or, alternatively, fasting glucose, when inputting the blood glucose information.

Figure 2:
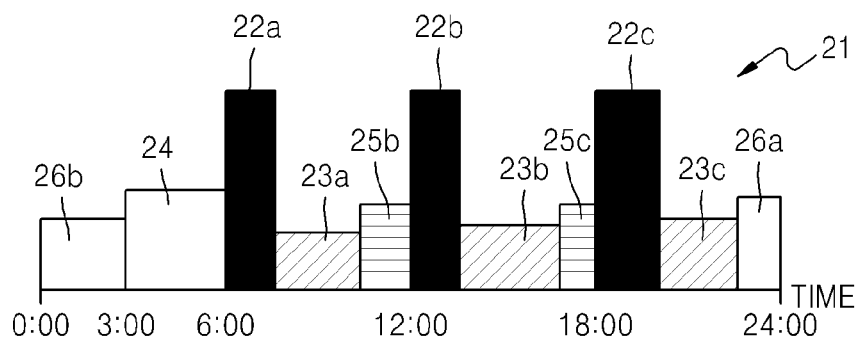
FIG. 2 is a timeline of a patient's meals versus mealtimes illustrating an embodiment of classifying groups of meals on the basis of the mealtimes.

FIG. 2 is a timeline of a patient's meals versus mealtimes illustrating an embodiment of classifying groups of meals on the basis of the mealtimes. More particularly, FIG. 2 shows a graph 21 illustrating groups classified on the basis of mealtimes. The graph 21 shows a breakfast 22a, a lunch 22b and a dinner 22c, and the grouping unit 321 classifies blood glucose information into groups according to the mealtime such as the breakfast 22a, the lunch 22b and the dinner 22c.

In general, an after-meal group is defined as blood glucose obtained within, for example, 4 hours after a meal, and a fasting group is defined as blood glucose obtained over 8 hours after a meal. These definitions are stored in the apparatus for providing blood glucose management information 300 as a basic setting, but may be altered or further defined by the user. According to the basic setting, if the breakfast 22a, the lunch 22b and the dinner 22c take about 1 hour each starting at 6:00, 12:00 and 18:00, respectively, the groups further include an after-breakfast group 23a, an after-lunch group 23b and an after-dinner group 23c which are within 4 hours of each respective meal, a fasting group 24 which is over 8 hours after a meal, a before-lunch group 25b and a before-dinner group 25c, and before-bedtime groups 26a and 26b.

When blood glucose information, such as a plurality of blood glucose levels and when the blood glucose levels are measured, as well as mealtimes are received from the user via the interface unit 310, the grouping unit 321 classifies the measured blood glucose levels into groups, as described above, by referring to the mealtimes and when the blood glucose levels are measured. The mealtimes and times when the blood glucose levels are measured are included in the blood glucose information. In an embodiment, the grouping unit 321 performs a grouping process by adding a tag, for example, indicating the grouping information to the measured blood glucose level. In addition, mealtimes, when the blood glucose levels are measured, and the measured blood glucose levels contained in the blood glucose information obtained from the user, and data to which grouping information is added, may be stored in the first database 131.

The grouping unit 321 groups the blood glucose levels included in the blood glucose information obtained from the user according to when the blood glucose levels are measured, relevant to mealtimes as factors influencing blood glucose, for example. The blood glucose level may vary according to when the blood glucose level is measured, e.g., whether the blood glucose level is measured while fasting, before a meal, after a meal, or before bedtime, for example. In addition, even though the blood glucose levels may be measured at the same times, the blood glucose levels may have different meanings according to the ingredients and amount of food consumed by the user, as well as use of blood glucose-controlling drug or insulin, for example. Thus, the grouping unit 321 groups the measured blood glucose levels using a number of factors influencing blood glucose, so that similar blood glucose information may be extracted. In addition, to accurately extract the similar blood glucose information, a reference of blood glucose information may be estimated.

Referring again to FIG. 1, the estimation unit 322 estimates a reference of each of the parameters relevant to the blood glucose information change pattern obtained using the measured blood glucose information from the user. In an embodiment, the parameters include various elements causing blood glucose information change patterns. For example, the parameter may be a period of time, after the subject has eaten, for the blood glucose level to reach a maximum, a blood glucose change according to an amount of carbohydrate contained in food, a period of time for the blood glucose level to reach a normal blood glucose level from the maximum, a period of time, after insulin infusion, for the blood glucose level to reach a normal blood glucose level, or a period of time after the administration of a blood glucose-controlling drug for the blood glucose to reach a normal blood glucose level. However, the parameters are not limited to the abovementioned examples, and may also include any element that may change the blood glucose information pattern, such as a blood glucose change according to an amount and/or intensity of exercise and a blood glucose change according to the intensity of stress, for example.

The estimation unit 322 may estimate a reference of each of the abovementioned parameters using the obtained blood glucose information. Since the blood glucose information includes when the subject eats, the amount of carbohydrate contained in food, when the blood glucose is measured, and the measured blood glucose level, for example, the estimation unit 322 may analyze the blood glucose change according to time when the blood glucose is measured to estimate the reference. In an embodiment, the reference of each of the parameters showing a blood glucose change pattern is estimated using a relationship between the time when the blood glucose level is measured, the time being contained in the blood glucose information, and the measured blood glucose level. In addition, the relationship between the time when the blood glucose level is measured and the measured blood glucose level is the degree of the measured blood glucose level with respect to time on the basis of time when a factor influencing blood glucose is generated. Thus, the estimation unit 322 estimates the reference, showing the degree of the blood glucose change according to time, by referring to the blood glucose information obtained from the user.

Figure 3:
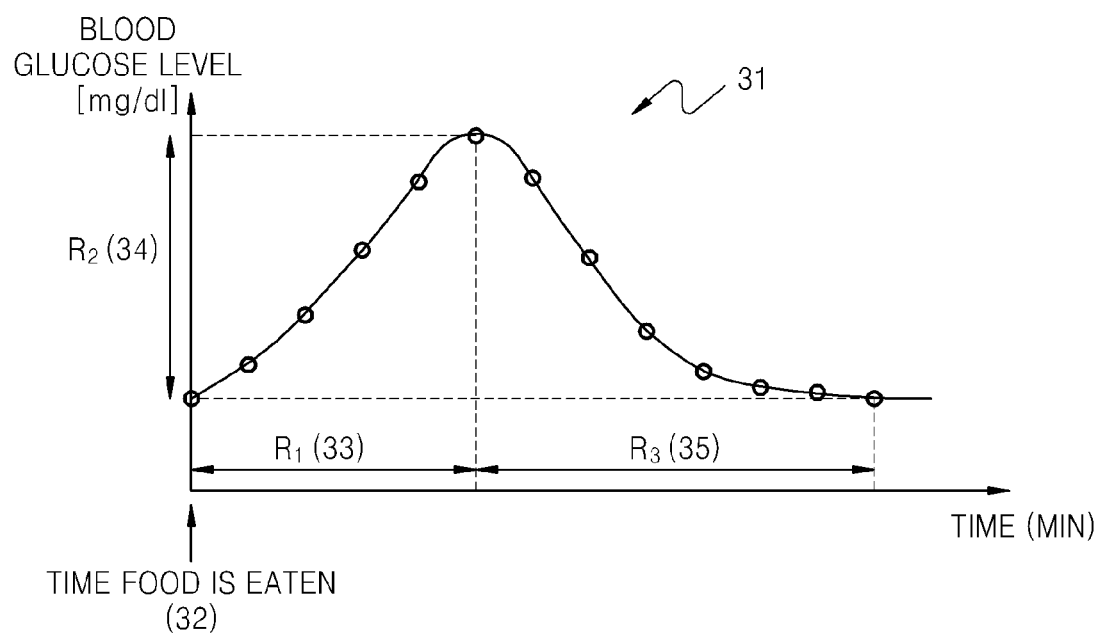
FIG. 3 is a graph of blood glucose level versus time illustrating an embodiment of blood glucose information obtained from a user.

FIG. 3 is a graph of blood glucose level, in milligrams per deciliter (mg/dl), versus time, in minutes (min), illustrating an embodiment of blood glucose information obtained from a user. Referring to FIG. 3, a graph 31 shows the blood glucose level with respect to a time the blood glucose level is measured. The interface unit 310 receives times when the subject eats 32, and blood glucose measured at times the subject eats 32, and at equal intervals, and the estimation unit 322 produces the graph 31 using the blood glucose information obtained from the interface unit 310 to estimate the references. In an embodiment, the intervals may vary, and may be, for example, 10 minutes or 20 minutes, although additional embodiments are not limited thereto.

In an embodiment, a period of time after the subject has eaten for the blood glucose level to reach a maximum is referred to as a first parameter for the blood glucose change pattern, and a first reference $R_1$ (33) of the first parameter may be a period from the time the subject eats 32 to a time when the blood glucose level reaches a maximum, as shown in FIG. 3. Thus, the estimation unit 322 estimates the first reference $R_1$(33) by analyzing the obtained blood glucose information and referring to the time the subject eats 32 and the time the blood glucose level reaches the maximum. For example, graph 31 shows blood glucose levels measured at 20 minute intervals, and the first reference $R_1(33)$ is therefore 100 minutes.

If a blood glucose change, based on an amount of carbohydrate contained in food, is referred to as a second parameter, a second reference $R_2(34)$ of the second parameter may be an increased blood glucose level, with respect to the amount of carbohydrate contained in food eaten by the subject. It will be noted that, since nutrients other than carbohydrate contained in food eaten by the subject influence the blood glucose after 3 to 4 hours after the subject eats the food, the blood glucose level is initially influenced by carbohydrates. Thus, the estimation unit 322 may estimate the second reference $R_2(34)$ by analyzing the obtained blood glucose information and referring to the amount of carbohydrate contained in the food the subject eats and the changed amount of blood glucose level. Specifically, for example, if the amount of carbohydrate is 10 grams (g), and the blood glucose level increases by 55 mg/dl, the second reference $R_2(34)$ may be about 5.5, as shown in FIG. 3. In another embodiment, the second reference $R_2(34)$ may also be estimated by referring to the amount of other nutrients other than carbohydrate and the changed amount of blood glucose level.

If a period of time for the blood glucose level to reach a normal blood glucose level from the maximum is referred to as a third parameter for the blood glucose change pattern, a third reference $R_3(35)$ of the third parameter may be a period of time from the maximum to a time point when the blood glucose level reaches the normal blood glucose level. Thus, the estimation unit 322 may estimate the third reference $R_3(35)$ by analyzing the obtained blood glucose information and referring to a time point when the blood glucose level reaches the maximum and the time point the blood glucose level reaches the normal blood glucose level. In an embodiment, a normal range may vary, for example, by about ±10 percent (%) of the blood glucose level before the subject eats. Specifically, for example, the graph 31 shows blood glucose levels measured at 20 minute intervals (indicated by the circles on the graph 31 in FIG. 3), the third reference $R_3(35)$ may be 140 minutes.

The first, second and third parameters described above are examples of the parameters showing the blood glucose change pattern, and the parameters used by the estimation unit 322 to estimate the references are not limited thereto.

Thus, in an embodiment, the estimation unit 322 estimates the reference showing the blood glucose change pattern by referring to the blood glucose information obtained from the user, and similar blood glucose information is accurately provided to the user. Accordingly, the accuracy of determining the similarity is improved, since the similarity is determined by comparing the estimated reference of each parameter when similar blood glucose information is searched for by using blood glucose information influenced by a number of factors. In addition, types of parameters and standards for the determination thereof may be added to further improve effectively managing blood glucose.

Referring again to FIG. 1, the estimation unit 322 estimates a reference of each of the parameters for each group classified by the grouping unit 321. As described above, the measured blood glucose levels may have different meanings, based on whether the subject eats or not, for example. Thus, the reference of each of the parameters for each group may be estimated by referring to the tag added by the grouping unit 321.

Accordingly, the grouping unit 321 classifies the blood glucose information based on the mealtime and adds the tag, including the classification information, to the blood glucose information, so that the estimation unit 322 may estimate the reference of the parameter of the classified group. Thus, since the apparatus for providing blood glucose management information 300 manages factors influencing the blood glucose information separately, based on the mealtime, for example, the accuracy of the search for blood glucose information similar to the received blood glucose information is increased.

In addition, if the blood glucose information obtained from the user is insufficient for estimating the reference, the estimation unit 322 estimates the reference by referring to the pieces of blood glucose information stored in the database module 130. Specifically, if the blood glucose levels contained in the blood glucose information obtained from the user are insufficient for estimating the reference, the estimation unit 322 estimates the reference by referring to the pieces of blood glucose information stored in the database module 130. For example, the estimation unit 322 generally uses blood glucose levels measured at 20 minute intervals to estimate the reference. However, if the blood glucose levels are measured at 1 hour intervals or, alternatively, are randomly measured after the subject eats, the estimation unit 322 estimates the reference by referring to data stored in the database module 130.

In an embodiment, the estimation unit 322 estimates the reference by referring to the blood glucose levels measured for an extended period of time, e.g., more than one interval (described above) or more. More particularly, the reference of each parameter may be estimated by referring to blood glucose levels and the amount of food intake measured for several days, for example, and may be stored in the database module 130. Thus, the estimation unit 322 may estimate the reference of the second parameter, for example, the blood glucose change according to the amount of carbohydrate contained in the food, by referring to the amount of carbohydrate contained in food measured for the extended period of time.

Figure 4:
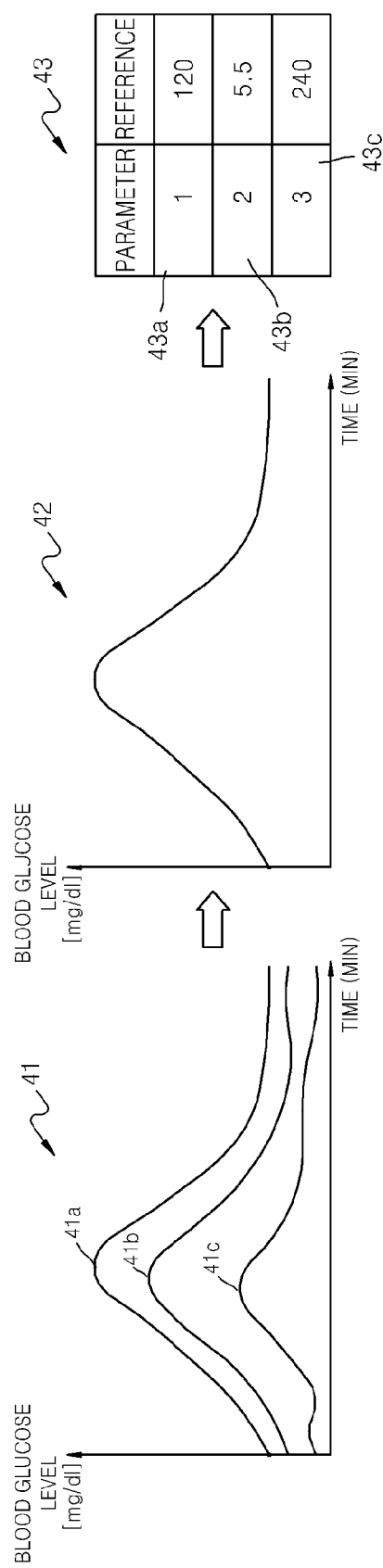
FIG. 4 includes graphs of blood glucose level versus time and a table for illustrating an embodiment of a method of estimating a reference using data obtained over a period of time.

FIG. 4 includes graphs of blood glucose level, in mg/dl, versus time, in minutes, and a table for illustrating an embodiment of a method of estimating a reference using data obtained over a period of time. More specifically, FIG. 4 shows a method of estimating a reference using data obtained for an extended period of time. FIG. 4 shows a graph 41 illustrating blood glucose changes according to the amount of carbohydrate intake, as a factor of increasing the blood glucose after the subject eats, a graph 42 illustrating a blood glucose change according to referential amounts of carbohydrate and a table 43 illustrating estimated references.

Graph 41, illustrating blood glucose changes according to the amount of carbohydrate intake, shows blood glucose levels measured after the subject eats, using data measured for an extended period of time. Thus, graphs 41a, 41b and 41c show the amount of blood glucose according to the amount of carbohydrate intake. Generally, as the amount of carbohydrate intake increases, the blood glucose increases. Since the amount of carbohydrate contained in food varies, the graph 41 illustrating blood glucose changes according to the amount of carbohydrate intake may be prepared by referring to data stored in the database module 130.

Graph 42, illustrating a blood glucose change according to referential amounts of carbohydrates, is a graph showing the degree of blood glucose change according to the referential amounts of carbohydrates (graph 41) illustrating blood glucose changes according to the amount of carbohydrate intake. Referring to graphs 41 and 42, the blood glucose change according to an average amount of carbohydrate that is consumed by the subject or according to the set referential amount of carbohydrate may be determined and shown. In an embodiment, a relationship in which the increase in the blood glucose is linearly proportional to the amount of carbohydrate may be used, but additional embodiments are not limited thereto.

Table 43 shows estimated references measured with respect to the parameters. As described above, when the period of time after the subject has eaten for the blood glucose level to reach a maximum is referred to as the first parameter, the blood glucose change according to the amount of carbohydrate contained in food intake is referred to as the second parameter, and the period of time for the blood glucose level to reach a normal blood glucose level from the maximum is referred to as the third parameter, the estimation unit 322 estimates the reference of the first parameter 43*a* as 120 minutes, the reference of the second parameter 43*b* as 5.5 mg/dl, and the reference of the third parameter 43*c* as 240 minutes by referring to graph 42, which illustrates a blood glucose change according to referential amounts of carbohydrate.

Figure 5:
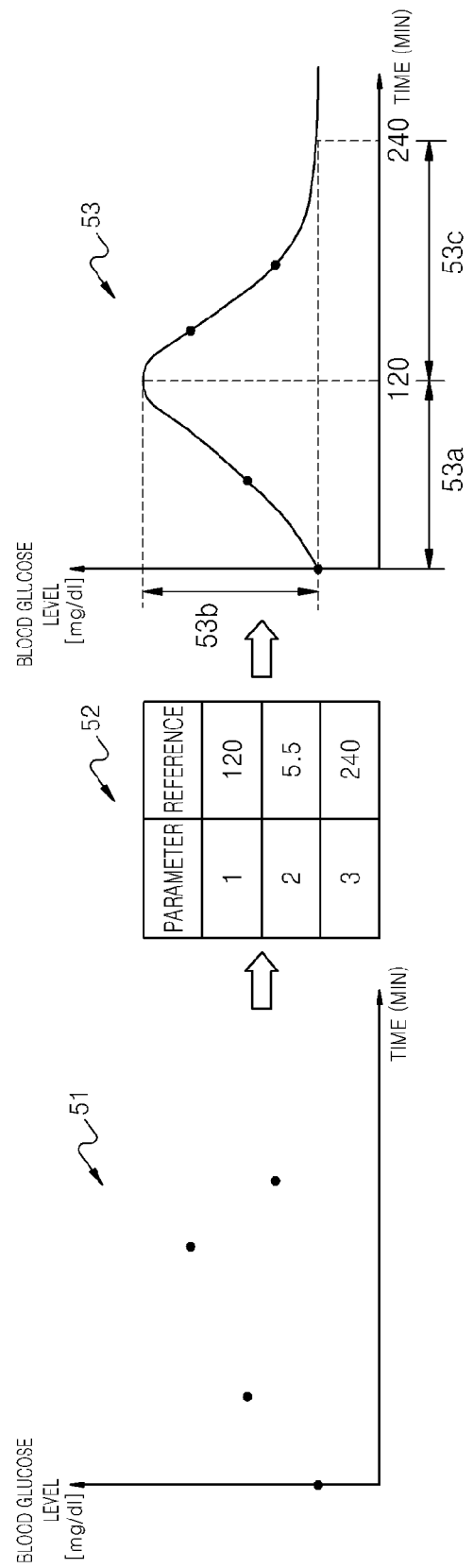
FIG. 5 includes graphs of blood glucose level versus time and a table for illustrating an embodiment of a method of estimating a reference using insufficient blood glucose information.

FIG. 5 includes graphs of blood glucose level versus time and a table, for illustrating an embodiment of a method of estimating a reference using insufficient blood glucose information. Specifically, FIG. 5 shows a graph 51 illustrating blood glucose information obtained from the user, a table 52 showing references stored in the database module 130 and a graph 53 for estimating the references.

As shown in graph 51, when insufficient blood glucose information is obtained from the user, the estimation unit 322 produces graph 53 for estimating references by referring to table 52, which includes references stored in the database module 130. In an embodiment, the table 52, including references stored in the database module 130, may be the table 43 (including estimated references shown in FIG. 4), but additional embodiments are not limited thereto. Thus, in an embodiment, the accuracy of the estimated reference increases, since the data is more similar to the blood glucose information obtained from the user.

Thus, in one or more example embodiments, the estimation unit 322 sets the first parameter 53*a*, e.g., the period of time after the subject has eaten for the blood glucose level to reach a maximum, as 120 minutes, the second parameter 53*b*, e.g., the blood glucose change according to the amount of carbohydrate contained in food intake, as 5.5 mg/dl, and the third parameter 53*c*, e.g., the period of time for the blood glucose level to reach a normal blood glucose level from the maximum, as 240 minutes, by referring to the table 52, to produce the graph 53 for estimating the references when insufficient blood glucose information is obtained from the user.

As described above, the estimation unit 322 estimates the reference of each of the parameters showing the blood glucose change pattern for the blood glucose information obtained from the user, and the accuracy of the search for blood glucose information similar to the received blood glucose information is substantially improved.

In an embodiment, the references estimated by the estimation unit 322 may be stored in the second database 132 of the database module 130 and may also be used in the determination of the similarity of the blood glucose change pattern in the determination unit 323.

Referring again to FIG. 1, the determination unit 323 compares the blood glucose information obtained from the user with the blood glucose information stored in the database module 130 to determine the similarity of the blood glucose change pattern. In addition, the determination unit 323 compares the reference estimated from the blood glucose information obtained from the user with the reference estimated from the blood glucose information stored in the second database 132 to determine the similarity therebetween, thereby substantially improving the accuracy of the similarity determination.

The determination of the similarity may be performed using various methods in different example embodiments. For example, the determination unit 323 may determine the similarity of the blood glucose change pattern by measuring distance. Specifically, the determination unit 323 calculates the distances of the estimated reference of each parameter to determine whether the similarity increases as the distance decreases. More specifically, the determination unit 323 determines the similarity by calculating the distance between the reference estimated from the blood glucose information obtained from the user and the reference stored in the second database 132. In this regard, the distance of each parameter may be calculated, or, alternatively, the distances of each group classified by the grouping unit 321 may be calculated.

The method of calculating the distance will now be described in further detail. If the reference of the first parameter of the blood glucose information obtained from the user is, for example, 120 minutes, and the reference of the first parameter stored in the second database 132 is, for example, 130 minutes, the distance between the reference of the first parameter of the blood glucose information obtained from the user and the reference of the first parameter stored in the second database 132 may be obtained by calculating the difference between the squares of 120 and the squares of 130, or by converting the 120 and 130 into a binary number (e.g., 0 and 1) and comparing digits thereof. For example, if the reference of the first parameter of the blood glucose information obtained from the user is 10, and the references of the first parameter stored in the second database 132 are 9 and 14, respectively. When calculating the difference between the squares of 10 and the squares of 9, or the difference between the squares of 10 and the squares of 14, it is obvious that the distance between 10 and 9 is smaller than the distance between 10 and 14. Thus, 9, which is the reference of the first parameter stored in the second database 132, is more similar with 10, which is the reference of the first parameter of the blood glucose information obtained from the user, than 14, which is the reference of the first parameter stored in the second database 132. However, the method of calculating the distances is not limited to the foregoing description.

In an exemplary embodiment, the determination unit 323 determines the similarity between the reference estimated from the blood glucose information obtained from the user and the reference estimated from the blood glucose information stored in the second database 132 using a weight applied to the parameters. Thus, a desired similarity may be easily extracted by calculating the distance and applying a weight to a parameter. Specifically, if the similar blood glucose information is extracted by applying a weight to the blood glucose change according to an insulin infusion, data desired by the user may be easily extracted by applying a relatively high weight to a parameter (relative to weights of other parameters) related to the type of insulin, an insulin infusion time and an amount of insulin, for example.

When a medical service is provided using various blood glucose information, data similar to that of a patient is searched. Even though a considerable amount of information is collected, it is necessary to extract accurate information from the collected information. Thus, similar blood glucose information may be easily extracted with substantially improved accuracy using the embodiments of the method of determining similarity described herein.

The determination unit 323 outputs the results of the similarity determination based on the calculated distance to the extraction unit 324 that extracts blood glucose information similar to the blood glucose information obtained from the user.

The extraction unit 324 extracts at least one piece of blood glucose information from the blood glucose information stored in the database module 130, based on the similarity determined by comparing the blood glucose information obtained from the user with the blood glucose information stored in the database module 130. As described in greater detail above, the extraction unit 324 extracts blood glucose information similar to the blood glucose information obtained from the user by referring to the calculated distance by comparing references by the determination unit 323.

More specifically, the extraction unit 324 extracts at least one piece of blood glucose information from the database module 130 in a decreasing order of distance, e.g., in an increasing order of similarity. The blood glucose information is extracted from at least one of the first database 131 and the second database 132, based on the result of similarity determination obtained based on the references stored in the second database 132. A predetermined number, e.g., 10, of blood glucose information may be extracted depending on the environment, or the blood glucose information having a distance less than a predetermined value, e.g., 2.0, may be extracted. The extracted blood glucose information may be provided to the user via the communications interface unit 110. In an embodiment, the blood glucose information is listed in an increasing order of similarity and is provided to the user, so that the user may select the blood glucose information having the highest similarity.

Thus, an embodiment of the apparatus for providing blood glucose management information 300 performs data mining using the blood glucose information stored in the database module 130, and the user may thereby search for blood glucose information having the highest similarity to the blood glucose information obtained from the user.

The prediction unit 325 predicts the amount of blood glucose change for the blood glucose information extracted by referring to the blood glucose information and blood glucose management information stored in the database module 130. If blood glucose information similar to that obtained from the user is extracted, the prediction unit 325 predicts the amount of the blood glucose change according to the factors influencing blood glucose of the blood glucose information obtained from the user by referring to the blood glucose management information corresponding to the extracted blood glucose information. Put another way, the prediction unit 325 refers to blood glucose information of another user having a similar blood glucose change pattern to that of the user and stored in the database module 130, and searches for a history having the similar pattern. Thus, the prediction unit 325 predicts the degree of blood glucose change when the user applies the same treatment, albeit of the other user, using an evidence-reference method.

The user may also input factors influencing blood glucose using the user terminal 200, or may manipulate the user interface unit 312 to search for the predicted amount of the blood glucose change. In an embodiment, the factors influencing the blood glucose may include insulin, exercise, amount of carbohydrate intake, blood glucose-controlling drug or stress, for example. In other words, the user may input the type, units, or sensitivity against insulin, time, duration or intensity of exercise, time and amount of carbohydrate intake, the type, units or time of the blood glucose-controlling drug, or time and duration of stress. As a result, the prediction unit 325 predicts the amount of blood glucose change according to the inputted factors. The predicted amount of the blood glucose is thus provided to the user via the interface unit 310.

Figure 6:
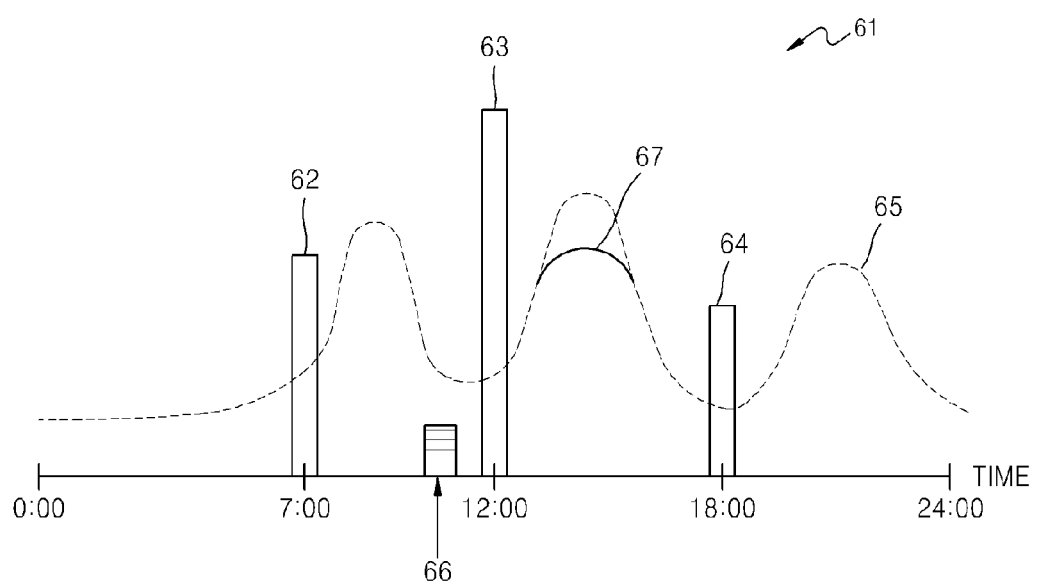
FIG. 6 is a timeline of a user's information illustrating an embodiment of a method of predicting a blood glucose change by referring to extracted blood glucose information.

FIG. 6 is a timeline of a user's information illustrating an embodiment of a method of predicting a blood glucose change by referring to extracted blood glucose information. Referring to FIG. 6, graph 61 shows a method of predicting the blood glucose level. In the blood glucose information obtained from the user shown in FIG. 6, mealtimes and amounts of carbohydrate intake during the mealtime are shown as bars. Specifically, breakfast time and amount of carbohydrate intake obtained during the breakfast are shown as a bar 62, a lunch time and amount of carbohydrate intake obtained during the lunch are shown as a bar 63, and a dinner time and amount of carbohydrate intake obtained during the dinner are shown as a bar 64.

In an embodiment, the mealtime and the amount of carbohydrate intake may be determined by the user to predict the amount of blood glucose change. In addition, when the prediction unit 325 predicts the amount of blood glucose change, the blood glucose information obtained from the user may not include a measured blood glucose level.

The amount of blood glucose change 65 shows the amount of blood glucose change predicted with reference to the database module 130. Thus, the prediction unit 325 refers to the reference extracted by the extraction unit 324 to predict the degree of blood glucose change. In addition, if the information about factors influencing blood glucose is inputted by the user, the prediction unit 325 predicts the degree of blood glucose change based on the input data.

Specifically, for example, the prediction unit 325 may predict another, or an additional, amount of blood glucose change 67 according to an insulin infusion 66. The graph shown in FIG. 6 may be displayed to the user using the user terminal 200 and/or the user interface unit 312.

Accordingly, in an embodiment, a user, e.g., a medical professional, may input blood glucose information of a subject and information regarding insulin and a drug to be administered to the subject to search for the amount of blood glucose change. Since the amount of blood glucose change is predicted by referring to the blood glucose information similar to that of the subject selected from the blood glucose information stored in the database module 130, the prediction is accurately performed. The prediction is thus efficiently applied to evidence-based medical science by which patients, such as the subject, are treated based on results of real treatments.

Referring again to FIG. 1, the data processing unit 320 refers to data stored in the database module 130 by the server management unit 330. The server management unit 330 operates with the database management unit 120 of the blood glucose information server 100 to renew data stored in the database module 130 or to extract information therefrom.

The server management unit 330 renews the blood glucose information stored in the database module 130 using the blood glucose information obtained from the user. In an embodiment, the renewal may include adding data to the database module 130 and also renewing the reference estimated using data measured over an extended period of time, as shown in FIG. 4.

As described above, the estimation unit 322 refers to estimated reference using data measured for an extended period of time when the reference is estimated using insufficient blood glucose information. In this regard, the referred reference is periodically renewed to improve the accuracy of the reference. Thus, the server management unit 330 observes the references stored for a predetermined period of time. If the renewal conditions are satisfied, the references may be renewed automatically or, alternatively, manually by the user using data measured for an extended period of time. The renewal may be performed when more than a predetermined number of the blood glucose information is obtained from the user or after a predetermined period of time after the previous renewal, for example.

In one or more embodiments, the server management unit 330 may renew a reference by replacing the reference with an average of the references for a predetermined period of time. For example, if the reference of the first parameter is renewed, the server management unit 330 refers to references of the first parameter for a predetermined period of time to calculate an average of the references estimated during the time period, and renew the reference with the average.

More specifically, for example, the estimation unit 322 refers to the reference estimated using data measured for an extended period of time and stored in the database module 130 to estimate the reference using insufficient blood glucose information. The server management unit 330 renews the reference estimated using the data measured for an extended period of time to improve the accuracy of the reference estimated by the estimation unit 322. In addition, the server management unit 330 may renew the reference using an adaptive method based on the time period corresponding to the insufficient blood glucose information. The server management unit 330 may use a window average in order to use the adaptive method. Thus, the server management unit 330 may renew the reference by adaptively calculating a new reference using a window for applying the transition of the change thereto.

As discusses above, the security processing unit 340 implements, e.g., performs, a security process on data outputted to the communications interface unit 311 and/or inputted from the communications interface unit 311. For example, the security processing unit 340 may encode data outputted to the communications interface unit 311, e.g., the blood glucose information of the subject or the blood glucose management information and, more particularly, may convert the subject identification information (such as the real name of the subject and the blood glucose management information) into symbols, such as numbers and characters, which are unrecognizable as the real name of the user and the associated blood glucose management information. The security processing unit 340 may also decode data inputted from the communications interface unit 311, e.g., encoded data received from the user terminal 200 or the blood glucose information server 100. In an additional embodiment, the apparatus for providing blood glucose management information 300 may not include the security processing unit 340.

Thus, the apparatus for providing blood glucose management information 300 operates with the user terminal 200 to systematically manage blood glucose information by searching for data having a similar blood glucose change pattern from the data collected by the blood glucose information server 100. In addition, to manage blood glucose information changing according to various factors, the amount of blood glucose change of a patient is predicted by referring to a predictable amount of the blood glucose change by factors such as exercise, diet and insulin, and a blood glucose managing service suitable for a patient is thereby provided.

In an embodiment, the blood glucose information server 100, the user terminal 200 and the apparatus for providing blood glucose management information 300 may include one or, alternatively, more than one, e.g., a plurality of, processors. Individual elements of the blood glucose information server 100, the user terminal 200 and the apparatus for providing blood glucose management information 300 may correspond to one or one of the plurality of the processors. The processor/processors may include an array of logic gates or a combination of a universal microprocessor and memories including programs that may be implemented in the universal microprocessor, but alternative embodiments are not limited thereto.

The graphs and tables shown in FIGS. 3 through 6 are provided for purposes of explanation, and it will be understood that the apparatus for providing blood glucose management information 300 may also process data without, or in addition to, the graphs and tables shown and described herein.

FIG. 7 is a flowchart illustrating an embodiment of a method of providing blood glucose management information. Referring to FIGS. 1 and 7, the method of providing blood glucose management information includes the following operations that are processed in the blood glucose management information providing system shown in FIG. 1. In one or more embodiments, the operations may be processed serially, in chronological order, but additional embodiments are not limited thereto.

In operation 701 (FIG. 7), the interface unit 310 (FIG. 1) obtains blood glucose information from the user. The blood glucose information may be received from the user terminal 200 via the communications interface unit 311, or may be directly inputted by the user via the user interface unit 312. In one or more embodiments, the input blood glucose information includes a blood glucose level, a time or times when the blood glucose is measured and mealtimes, for example, as described in greater detail above. Specifically, for example, the blood glucose information may include a time of 7 a.m. (7:00) when eating is finished and blood glucose information measured at 7 a.m. when eating is finished, at 7:10 a.m. (7:10), and at 7:20 a.m. (7:20), and the amount of carbohydrate intake obtained from the meal.

In operation 702, the grouping unit 321 classifies blood glucose information obtained from the user into several groups, according to times the blood glucose is measured, which are also related to times at which factors influencing blood glucose are generated. Specifically, the blood glucose information may be classified into groups by adding a tag indicating an after-breakfast group, for example.

In operation 703, the estimation unit 322 estimates a reference of each of the parameters, showing a blood glucose change pattern of each group. In an embodiment, the reference may be estimated using a relationship between the time the blood glucose is measured and the measured blood glucose level.

In operation 704, the determination unit 323 compares the reference estimated from the blood glucose information obtained from the user with the reference estimated from the blood glucose information stored in the database module 130 to determine a similarity therebetween. In an embodiment, the similarity may be determined by calculating the distance of the references of the same parameter used to determine the similarity, as described above.

In operation 705, the extraction unit 324 extracts at least one piece of blood glucose information from the blood glucose information stored in the database module 130 based on the determined similarity. The extraction unit 324 extracts blood glucose information in a decreasing order of the distance, e.g., in an increasing order of the similarity, based on the determined similarity.

In operation 706, the prediction unit 325 predicts the amount of blood glucose change from blood glucose information extracted by referring to the blood glucose information stored in the database module 130. For example, the prediction unit 325 may predict the amount of blood glucose change according to factors influencing blood glucose, such as the insulin infusion, by referring to the database module 130.

In operation 707, the interface unit 310 provides blood glucose management information corresponding to the extracted blood glucose information to the user. The blood glucose management information is displayed to the user via the user interface unit 312 and/or to the user terminal 200 via the communications interface unit 311. In an embodiment, the blood glucose management information indicates detailed information corresponding to blood glucose information similar to blood glucose information obtained from the user. Thus, the blood glucose information accumulated during the period of managing blood glucose is provided to the user.

It will be noted that operations 701 through 703 are performed to further increase an accuracy of extracting similar blood glucose management information, and thus may be omitted in another additional embodiment. In addition, the amount of blood glucose change may be predicted (e.g., in operation 706) only upon request of the user.

Thus, a user, such as a medical professional, may provide an appropriate prescription to another user, such as a patient, by referring to blood glucose information similar to that of the patient using the blood glucose management information providing system. Appropriate blood glucose information may be searched for, not only based on text-based contents, but also (or exclusively) based on intelligence that is collective and obtained from other sources, such as corporations and/or a plurality of individuals in addition to the subject.

In addition, since it is difficult to continuously measure blood glucose, and since blood glucose levels have different meanings according to mealtimes, for example, and insulin sensitivity or carbohydrate sensitivity also varies according to physical characteristics of the subject, similarity may be determined by estimating a reference of a parameter for each group using the blood glucose management information providing system, and thus blood glucose information similar to that of the subject may be more accurately extracted. Additionally, the patient may therefore receive an appropriate treatment based on evidence-based medicine, by referring to blood glucose management information of the extracted blood glucose information, so that the health of the patient may be substantially improved.

As described herein, according to one or more example embodiments, blood glucose management information corresponding to blood glucose information having a similar blood glucose change pattern is provided to a user. Thus, the user provides and/or receives an appropriate treatment for the blood glucose management by referring to the blood glucose management information.

In addition, other embodiments of the present invention can also be implemented through computer-readable code/instructions in/on a medium, e.g., a computer readable medium, to control at least one processing element to implement any of the above-described embodiments. The medium can correspond to any medium/media permitting the storage and/or transmission of the computer-readable code.

The computer-readable code can be recorded/transferred on a medium in a variety of ways, with examples of the medium including recording media, such as magnetic storage media, e.g., read-only memory ("ROM"), floppy disks and hard disks, as well as optical recording media such as compact-disc read-only memory (CD-ROM) or digital versatile discs ("DVDs"), and transmission media, such as wired or wireless Internet transmission media. Thus, the medium may be a defined and measurable structure including or carrying a signal or information, such as a device carrying a bitstream, although additional embodiments are not limited thereto. The media may also be a distributed network, so that the computer readable code is stored/transferred and executed in a distributed fashion. Furthermore, the processing element could include a processor or a computer processor, and processing elements may be distributed and/or included in a single device. A computer that reads and executes the computer-readable code may be a specific- or general-use computer or, alternatively, a combination thereof.

While the general inventive concept has been particularly shown and described with reference to example embodiments thereof, it will be understood by those of ordinary skill in the art that various changes in form and details may be made therein without departing from the spirit or scope of the present invention as defined by the following claims.

What is claimed is:

1. A method of providing blood glucose management information, the method comprising:
   determining, by using at least one processor, a similarity of a blood glucose change pattern of a user by comparing blood glucose information obtained from the user and blood glucose information stored in a database;
   extracting at least one piece of blood glucose information from the blood glucose information stored in the database according to the determined similarity; and
   providing the blood glucose management information, which corresponds to the extracted blood glucose information, to the user so that the health of the user may be substantially improved,
   wherein the determining of the similarity comprises:
   classifying the blood glucose information obtained from the user into groups according to a time when the blood glucose level of the user is measured which is relevant to a time when a factor influencing blood glucose is generated; and
   comparing a first reference estimated from the blood glucose information obtained from the user with a second reference estimated from the blood glucose information stored in the database with respect to each of the classified groups,
   wherein the first reference comprises a representative value indicating one of the blood glucose change patterns of the user, and
   the first reference is estimated from a relationship between the time when the blood glucose level of the user is measured and the blood glucose level.

2. The method of claim 1, wherein
   a reference of each parameter of a plurality of parameters showing the blood glucose change pattern is estimated using the relationship between the time when a blood glucose level of the user is measured and the measured blood glucose level, and
   the time when the blood glucose level of the user is measured is included in the blood glucose information obtained from the user.

3. The method of claim 2, wherein the relationship between the time when the blood glucose level is measured and the measured blood glucose level is a change degree of the measured blood glucose level, with respect to time, based on the time when a factor which influences blood glucose is generated.

4. The method of claim 2, wherein the determining the similarity further comprises determining a similarity between the first reference estimated from the blood glucose information obtained from the user and the second reference estimated from the stored blood glucose information using a weight applied to each of the parameters.

5. The method of claim 1, wherein the reference estimated from the blood glucose information obtained from the user is estimated by referring to the stored blood glucose information.

6. The method of claim 1, wherein the determining the similarity further comprises comparing the first reference estimated from the blood glucose information obtained from the user with the second reference estimated from the stored blood glucose information for each of the groups.

7. The method of claim 1, wherein the stored blood glucose information is renewed using the blood glucose information obtained from the user.

8. The method of claim 1, wherein
the determining the similarity comprises calculating a distance between the first reference estimated from the blood glucose information obtained from the user and the second reference estimated from the stored blood glucose information,
the extracting the at least one piece of blood glucose information comprises referring to the distance calculated based on a result of the determining the similarity, and
the providing the blood glucose management information comprises providing blood glucose management information, corresponding to blood glucose information selected by the user from the extracted blood glucose information, to the user.

9. The method of claim 1, wherein the providing the blood glucose information comprises providing an amount of blood glucose change, predicted from the extracted blood glucose information by referring to the stored blood glucose information.

10. The method of claim 1, further comprising performing a security process on the blood glucose management information corresponding to the extracted blood glucose information to generate security-processed information,
wherein the providing the blood glucose management information comprises providing security-processed information.

11. A non-transitory computer program product comprising a computer-readable computer program for executing a method of providing blood glucose management information and instructions for causing a computer to implement the method, the method comprising:
determining a similarity of a blood glucose change pattern of a user by comparing blood glucose information obtained from the user and blood glucose information stored in a database;
extracting at least one piece of blood glucose information from the blood glucose information stored in the database according to the determined similarity to generate extracted blood glucose information; and
providing the blood glucose management information, which corresponds to the extracted blood glucose information, to the user,
wherein the determining of the similarity comprises:
classifying the blood glucose information obtained from the user into groups according to a time when the blood glucose level of the user is measured which is relevant to a time when a factor influencing blood glucose is generated; and
comparing a first reference estimated from the blood glucose information obtained from the user with a second reference estimated from the blood glucose information stored in the database with respect to each of the classified groups, wherein the first reference comprises a representative value indicating one of the blood glucose change patterns of the user, and
the first reference is estimated from a relationship between the blood glucose level of the user and the time when the blood glucose level of the user is measured.

12. An apparatus which includes at least one processor and provides blood glucose management information, the apparatus comprising:
a grouping unit configured to classify blood glucose information obtained from the user into groups according to a time when the blood glucose level of the user is measured which is relevant to a time when a factor influencing blood glucose is generated;
a determination unit configured to determine a similarity of a blood glucose change pattern of a user by comparing a first reference estimated from the blood glucose information obtained from the user and a second reference estimated from blood glucose information stored in a database with respect to each of the classified groups;
an extraction unit configured to extract at least one piece of blood glucose information from the pieces of blood glucose information stored in the database according to the similarity and generates extracted blood glucose information;
an interface unit configured to provide the blood glucose management information, which corresponds to the extracted blood glucose information, to the user; and
an estimation unit configured to estimate the first reference and the second reference, and estimate the first reference from a relationship between the blood glucose level of the user and the time when the blood glucose level of the user is measured,
wherein the first reference comprises a representative value indicating one of the blood glucose change patterns of the user.

13. The apparatus of claim 12, wherein
the estimation unit is further configured to estimate the first reference of each parameter of a plurality of parameters showing a blood glucose change pattern for the blood glucose information obtained from the user.

14. The apparatus of claim 13, wherein
the time when the blood glucose level of the user is measured is included in the blood glucose information obtained from the user.

15. The apparatus of claim 12, wherein
the estimation unit is further configured to estimate the first reference of each parameter of a plurality of parameters showing a blood glucose change pattern for each of the groups,
wherein the determination unit is configured to determine the similarity by comparing the first reference estimated from the blood glucose information obtained from the user with the second reference estimated from the stored blood glucose information for each of the groups.

16. The apparatus of claim 12, further comprising a server management unit configured to renew the stored blood glucose information using the blood glucose information obtained from the user.

17. The apparatus of claim 12, further comprising a prediction unit configured to predict an amount of blood glucose change from the extracted blood glucose information by referring to the stored blood glucose information and generate a predicted amount of blood glucose change,
wherein the interface unit further provides the predicted amount of blood glucose change.

18. The apparatus of claim 12, wherein the interface unit comprises:
- a user interface configured to receive blood glucose information from the user and output the blood glucose management information corresponding to the extracted blood glucose information to the user; and
- a communications interface unit configured to at least one of receive the blood glucose information from a user terminal and transmit the blood glucose management information corresponding to the extracted blood glucose information to the user terminal.

* * * * *